United States Patent [19]
Loberg et al.

[11] 4,017,596
[45] Apr. 12, 1977

[54] RADIOPHARMACEUTICAL CHELATES AND METHOD OF EXTERNAL IMAGING

[75] Inventors: Michael Dewey Loberg, Baltimore; Patrick Stephen Callery, Timonium; Malcolm Cooper, Reisterstown, all of Md.

[73] Assignee: Research Corporation, New York, N.Y.

[22] Filed: Sept. 2, 1975

[21] Appl. No.: 609,545

Related U.S. Application Data

[63] Continuation-in-part of Ser. No. 555,037, March 3, 1975, abandoned.

[52] U.S. Cl. .................................. 424/1; 250/303; 260/429 R; 260/534 E
[51] Int. Cl.² ................ A61K 43/00; A61K 29/00; C07C 101/02; G01T 1/16
[58] Field of Search ........... 424/1; 260/283, 429 R, 260/429 J, 561, 514, 526 S, 534 E

[56] References Cited
UNITED STATES PATENTS

| | | | |
|---|---|---|---|
| 3,466,361 | 9/1969 | Richards et al. | 424/1 |
| 3,728,351 | 4/1973 | Counsell et al. | 424/1 |

OTHER PUBLICATIONS

Burdine, Jr. et al., Journal of Nuclear Medicine, vol. 10, No. 6, June, 1969, pp. 290–293.
Hosain, et al., British Journal Of Radiology, vol. 45, No. 537, Sept. 1972, pp. 677–679.

*Primary Examiner*—Richard D. Lovering
*Assistant Examiner*—Christine M. Nucker
*Attorney, Agent, or Firm*—Cameron, Kerkam, Sutton, Stowell & Stowell

[57] ABSTRACT

A chelate of technetium-99m, cobalt-57, gallium-67, gallium-68, indium-111 or indium-113m and a substituted iminodiacetic acid or an 8-hydroxyquinoline useful as a radiopharmaceutical external imaging agent. The invention also includes preparative methods therefor.

13 Claims, 5 Drawing Figures

Tc 99m    I 131
Chelate   Rose Bengal

RADIOPHARMACEUTICAL CHELATES AND METHOD OF EXTERNAL IMAGING

BACKGROUND OF THE INVENTION

This is a continuation-in-part application of our copending U.S. application Ser. No. 555,037, filed on Mar. 3, 1975, now abandoned.

Radiopharmaceutical imaging agents have been utilized heretofore for the external imaging of various portions of the anatomy. Only radiopharmaceuticals which emit gamma-photons are suitable for this utility. The field of application is restricted due to the fact that of the radionuclides which emit gamma rays, very few meet the additional requirements imposed by the inherent limitations of exiting imaging systems and by the necessity of keeping the radiation dose as low as possible. Among these requirements are the need for a simple gamma spectrum, a high yield of photons having an energy sufficiently low to permit effective collimation and efficient detection and a half-life sufficiently short to permit the admininstration of millicurie quantites without an excessive post-test radiation dose.

The usual method of external imaging generally comprises labeling or tagging an organic compound suitable for administration to a patient with a suitable radioisotope. More particularly, a biological agent known to localize in the particular organ or anatomical section to be imaged is labeled to a small extent with a radioisotope. The thus labeled biological agent then permits external imaging of the desired organ utilizing conventional radio scanning techniques.

The problems associated with prior art attempts in this direction center mainly on combining the requirements (1) that the biological agent be specific to the organ to be imaged (2) that a suitable radionuclide be employed as the labeling agent (3) that the labeled agent is sufficiently stable in vivo to permit effective imaging and (4) that the labeled biological agent retains its organ specificity.

It is an object of the present invention to provide a radiolabeled biological agent having a high degree of in vivo stability and which is highly organselective. It is a further object of the invention to provide a method of external imaging employing said agent. It is still a further object of the invention to provide a method for the preparation of said agent.

SUMMARY OF THE INVENTION

The above objects are achieved by providing a radiolabeled diagnostic agent which combines the high target organ specificity of various drugs and biochemicals with the excellent nuclear imaging properties of the radiometals technetium-99m, cobalt-57, gallium-67, gallium-68, indium-111 or indium-113m.

The invention is predicated on the discovery that chelates of the above radiometals with a substituted iminodiacetic acid or an 8-hydroxyquinoline have a high degree of in vivo stability, are highly specfic to certain organs or anatomical sections and posses excellent nuclear imaging properties.

The above chelates may be prepared by reacting the desired radio-isotope with the chelating agent.

DETAILED DESCRIPTION OF THE INVENTION

Figure 1:
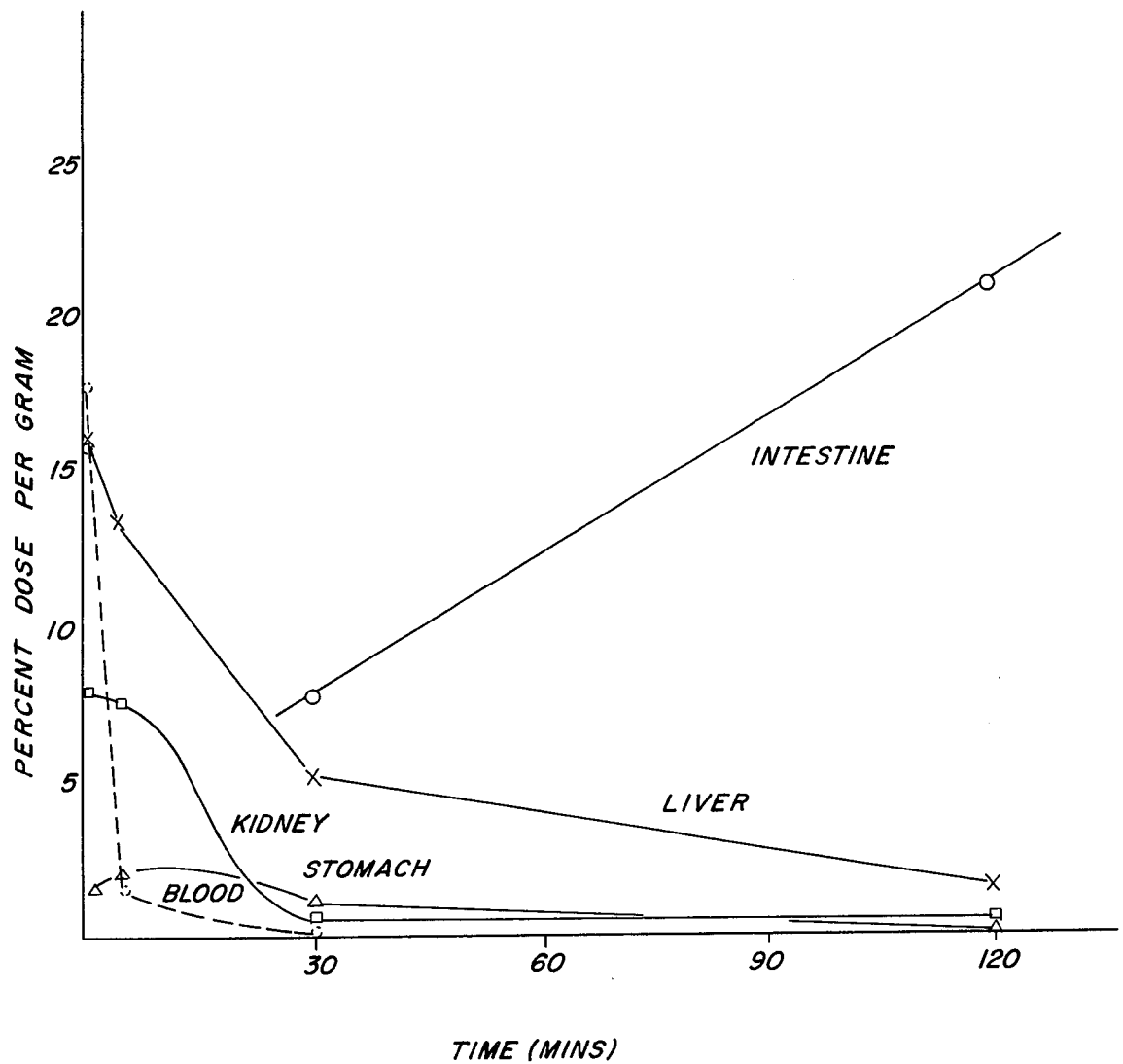
FIG. 1 is a graph showing in vivo distribution of a product according to the invention.

Technetium-99m is commercially available either from an isotope generator as a daughter product of molybdenum-99 or as a direct product from a commercial supplier. It is also available as a solvent extraction product from molybdenum-99 solutions generally as alkali metal pertechnetate solutions at 5-100 mCi. A further discussion of preparative methods appears in U.S. Pat. Nos. 3,468,808 and 3,382,152.

The technetium-99m chelate is most preferably prepared by reducing a solution of a pertechnetate, e.g., an alkali metal pertechnetate in the presence of the chelating agent. The reduction is preferably effected utilizing stannous chloride as a reducing agent. Any suitable reducing agent may be employed including other stannous salts such as stannous pyrophosphate. As a result of this reduction step, the product will also contain a significant proportion of the stannous chelate. It is to be understood that the present invention includes the product mixture containing both the radiometal chelate and the corresponding stannous chelate.

Indeed, the composition of the invention is most conveniently provided as a sterile kit consisting of non-radioactive chemicals for mixing with the radiometal source prior to use. The kit preferably contains a stannous salt solution, pH buffer solution or combinations thereof. Using sterile reagents and aseptic techinques, the respective solutions would be mixed with each other in any desired order and then with the radiometal source solution. The resulting solution containing the radiometal chelate, te stannous chelate and any free chelate may then be employed directly for imaging purposes.

Generally, a solution adapted for intravenous administration containing up to 15 mCi of radioactivity is administered to the patient. Generally , this may be accomplished by administering 0.2–1 ml of a solution containing from about 2 to about 100 mg of combined chelate product. Radioassay of the radio-isotope in the desired organ may be accomplished utilizing equipment, such as a scintillation camera, etc.

Organ specificity is determined by the particular chelating agent employed. All of the chelates according to the present invention, however, are cleared through either the kidneys or liver. Therefore, the chelates of the above radiometals with most substituted iminodiacetic acids and 8-hydroxyquinolines may be utilized for the imaging of these organs.

Preferably, the chelating agents are of the formulae

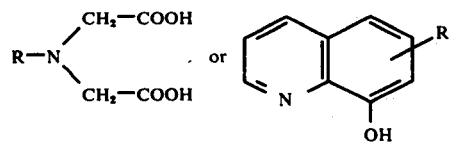

wherein R may be alkyl of up to about 24 carbon atoms preferably about 14 carbon atoms, alkenyl, aryl alkyl or cyclo-aliphatic groups substituted with halogen, hydroxy, carboxy, nitro, amino, keto or heterocyclic groups. The groups may be interrupted by ether or thio-ether linkages.

The most preferred chelating agents are the substituted iminodiacetic acid and 8-hydroxyquinoline analogs of drugs and biochemicals whose organ specificity characteristics are known.

Other specific chelating agents suitable for use in the practice of the invention are N-methyl-iminodiacetic acid, N-(10-carboxydecyl) iminodiacetic acid, N-[N'-(2,6-dimethylphenyl) carbamoylmethyl] iminodiacetic acid, N-(o-bromobenzyl) iminodiacetic acid, N-[3-(1-naphthyloxy)-2-hydroxypropyl] iminodiacetic acid, nitrilotriacetic acid, or 5,7-diiodo-8-hydroxyquinoline.

It is to be understood that the term "substituted iminodiacetic acid" is intended to include those compounds wherein R in the above structural formula combines with each methylene group to form a heterocyclic ring. An example of such an acid is 2,6-pyridinedicarboxylic acid.

The gallium and indium chelates ae prepared by the addition of either $GaCl_3$ or indium chloride in 0.05 M HCl to the appropriate chelating agent at pH 3.5. After a 25-minute incubation period, the pH is raised to between 5 and 7.

The invention is illustrated by the following non-limiting examples.

EXAMPLE 1

2 grams (0.01 moles) of alpha-chloro-2,6-acetylxylidine and 2 grams (0.01 moles) of iminodiacetic acid (disodium salt) were refluxed in 200 ml of a 3:1 $ETOH/H_2O$ mixture for 48 hours. The mixture was evaporated to dryness to yield a yellow residue. 25 ml of $H_2O$ were added to the residue. That which failed to go into solution was collected by vacuum filtration. To the filtrate concentrated hydrochloric acid was added drop-wise and the pH monitored. At pH 3 the clear solution became cloudy and was cooled overnight. An off-white precipitate was collected which was recrystallized from boiling water. The product was identified as N-[N'-(2,6-dimethylphenyl) carbamoylmethyl] iminodiacetic acid. m.p. 201°–203°. Percent yield 20% of theoretical.

| NMR: | DMSO-$d_6$ | $\delta = 7.11$ (s,3, aromatic protons) |
| --- | --- | --- |
| | | $\delta = 3.63$ (s,4,$CH_2$—COO—) |
| | | $\delta = 3.57$ (s,2,—$CH_2$—N<) |
| | | $\delta = 2.20$ (s,6,$CH_3$) |
| CHN: | 57.13 C 6.16 H 9.52N Theor | |
| | 57.10 C 6.23 H 9.43N Exp | |

EXAMPLE 2

The N-[N'-(2,6-dimethylphenyl) carbamoylmethyl] iminodiacetic acid prepared according to Example 1 in an amount of 150 mg (0.51 mmoles) was dissolved in 3 ml of 0.1 N NaOH. The pH of the solution was adjusted to 3.5 with 1 N HCl. Extra 0.1N NaOH was added thereto to compensate for the acidic $SnCl_2$ solution which follows. 0.3 cc of a solution of $SnCl_2$ (20 mg. 0.11 mmole in 10 ml of 1 N HCl) was added. After a five-minute wait 80 microcuries of technetium-99m as sodium pertechnetate was added. The product was chromatographed in saline and recorded on a radiochromatogram scanner. The resulting graph showed a peak at the solvent front, $R_f = 1$ due to the chelated compound. There was little colloid formation. There was substantially no free technetium-99m ($TR_f = .75$).

EXAMPLE 3

Methyl iminodiacetic acid in an amount of 150 mg was dissolved in 3 ml of 0.1 N NaOH. The pH of the solution was adjusted to 3.5 with 1 N HCl. Extra 0.1 N NaOH was added thereto to compensate for the acidic $SnCl_2$ solution which follows. 0.3 cc of a solution of $SnCl_2$ (20 mg. 0.11 mmole in 10 ml of 1 N HCl) was added. After a five-minute wait 80 microcuries of technetium-99m as sodium pertechnetate was added. The product was chromatographed in saline and recorded on a radiochromatogram scanner. The resulting graph showed a peak at the solvent front, $R_f = 1$ due to the chelated compound. There was little colloid formation. There was substantially no free technetium-99m ($TR_f = 0.75$).

EXAMPLE 4

2 $\mu$ Ci (technetium-99m) of the product of Example 2 were injected intravenously into mice. The animals were sacrificed serially after injection and the activities in major organs were determined by counting multiple samples from each organ in a scintillation counter. The in vivo distribution of the product of Example 2 in the mice were plotted as a function of time as shown in FIG. 1.

EXAMPLE 5

Figure 2:
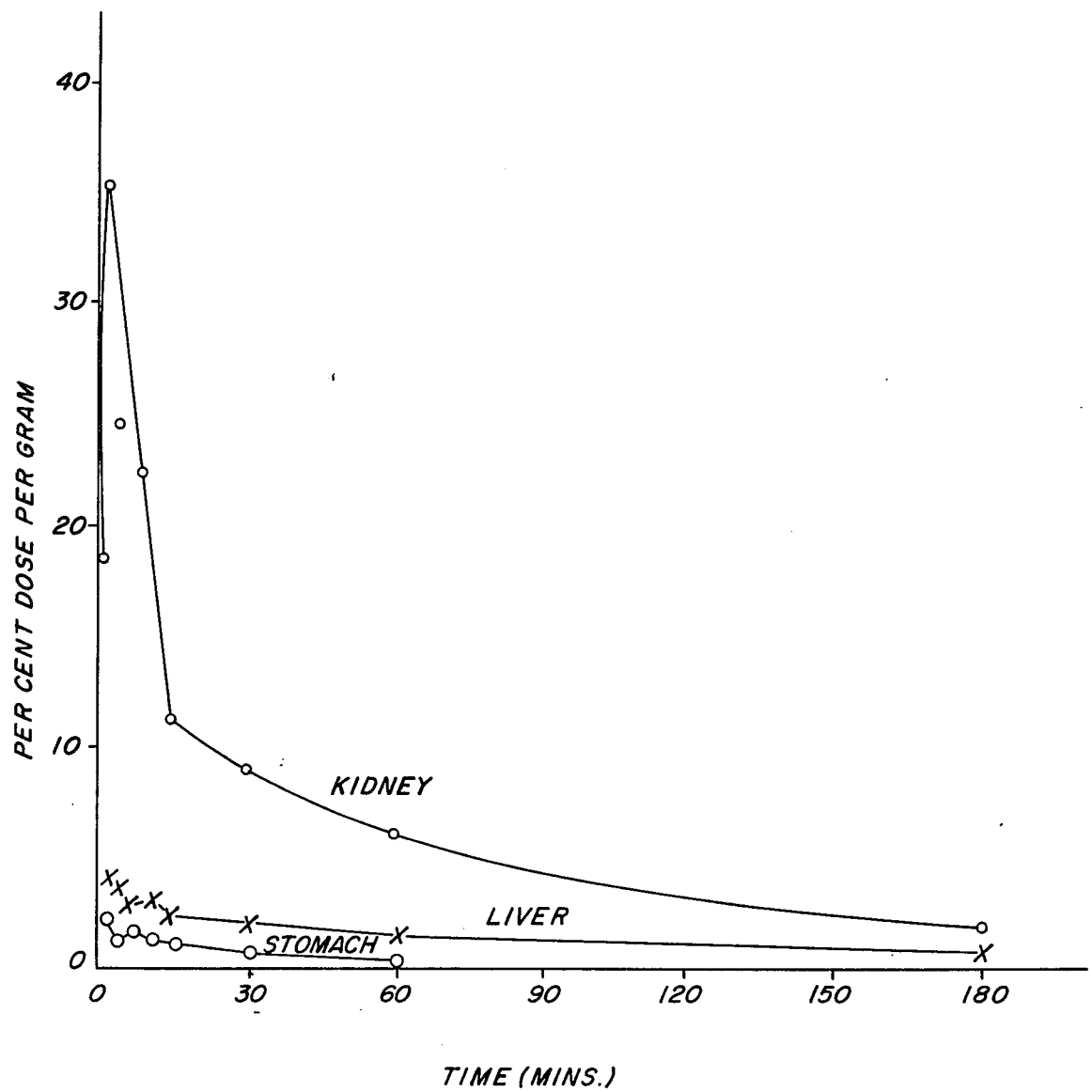
FIG. 2 is a graph showing in vivo distribution of another product according to the invention.

The procedure of Example 4 was followed utilizing the product of Example 3. The in vivo distribution of this product in mice as a function of time were plotted as shown in FIG. 2.

EXAMPLE 6

Figure 3:
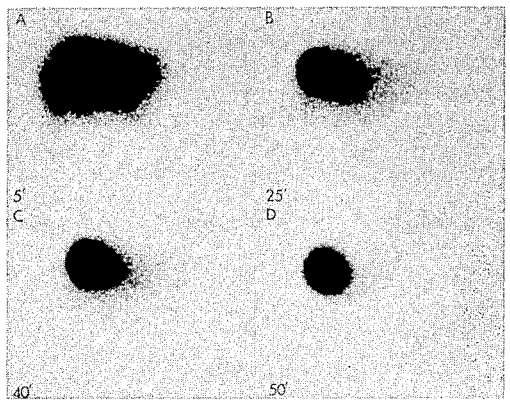
FIG. 3 is an anterior imaging study, after injection of a product according to the invention.
Figure 4:
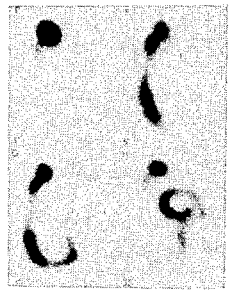
FIG. 4 is an anterior imaging study at a later time than FIG. 3.

4 mCi (technetium-99m) of the product of Example 2 were intravenously injected into laboratory dogs. One animal was selected for imaging at various time intervals utilizing a scintillation camera. Camera images were obtained in multiple exposures and demonstrated the localization of technetium-99m in the liver. See FIG. 3, which depicts anterior imaging studies and demonstrates the rapid uptake by the liver which is clearly identified at 5 minutes. (Frame A). The gall bladder appears as a cold defect. Sequential images taken at 25, 40 and 50 minutes are shown in Frames B, C, and D, in which clearance from the liver is demonstrated with progressive accumulation of the radiopharmaceutical in the gall bladder. Less than 10% and 3% of the injected dose remained in the blood at 10 minutes, respectively. Sufficiet cholecystokinin was injected into the dog intravenously to effect contraction of the gall bladder. Sequential studies revealed radiopharmaceutical activity progressing through the small intestines, seen in FIG. 4. Within 1 minute of the injection of cholecystokinin the technetium-99m labeled product is seen leaving the gall bladder (Frame E). Frames F, G and H taken at 5, 10 and 35 minutes show a bolus of activity moving progressively through a small intestine. The images were obtained using a gamma scintillation camera (Pho Gamma III) and a parallel hole high sensitivity collimator.

EXAMPLE 7

Figure 5:
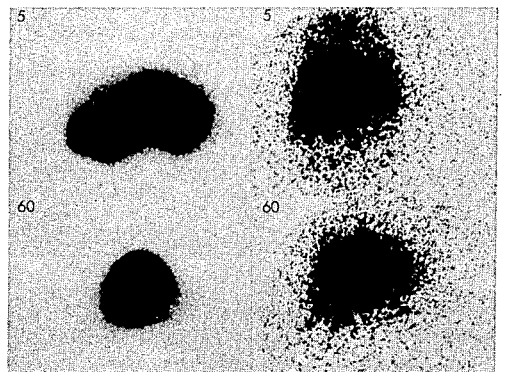
FIG. 5 is an imaging study of a Rose Bengal product vs. a product according to the invention.

The procedure of Example 6 was carried out and the results compared with those obtained following injection of the same dog at a later time with I-131 Rose Bengal. Both before and after plasma loading with bromosulphthalein (BSP) to simulate hyperbilirubinemia, BSP levels of 4–7 mg percent did not substantially alter the plasma clearance or imaging characteristics of the techmetium-99m labeled product. These images were of much better quality when compared to those obtained subsequently in the same dog using I-131 Rose Bengal, as shown in FIG. 5.

EXAMPLE 8

The procedure of Examples 2 and 3 was followed to prepare the technetium-99m chelate of 8-hyroxyquinoline, employing a 7 m-molar solution of 8-hydroxyquinoline and an acidic stannous chloride reducing solution. The chelate was recovered by chloroform extraction at a yield greater than 90%.

Biodistribution studies were undertaken utilizing the procedure of Example 4. 2 $\mu$ Ci (technetium-99m) of the above chelate were injected intravenously into 25 g mice. The animals were sacrificed after 60 minutes and the activities in major organs were determined by counting multiple samples from each organ in a scintillation counter. It was determined that on an average, 40% of the injected dose appeared in the liver and 20% in the intestines.

EXAMPLE 9

The gallium-67 chelate of 8-hydroxyquinoline was prepared by adding $Ga^{67}$ $Cl_3$ in 0.05M HCl to an aqueous 7 m-molar 8-hydroxyquinoline solution having a pH of 3.5. Following a 25 minute incubation period the pH is raised to 6. Chloroform extraction of the reaction product produced a >90% yield of the chelate. Biodistribution studies were undertaken according to the procedure outlined in Example 8. Following intravenous injection of the chelate into 25 g mice, 25% of the injected dose was found in the liver, 13% in the intestines and 20% in the blood after 60 minutes.

EXAMPLE 10

The technetium-99m chelate of nitrilotriacetic acid was prepared according to the stannous chloride reduction method outlined in Examples 2, 3 and 8. The chelate is water-soluble with >95% migration in saline employing paper chromatography. Biodistribution studies were carried out according to the procedure outlined in Example 8. The chelate was found to rapidly clear through the kidneys to urine (40% eliminated in urine after 60 minutes) with less than 5% of the injected dose found in the liver and intestines.

EXAMPLE 11

The cobalt-57 chelate of N-[N'-(2,6-dimethylphenyl) carbamoylmethyl] iminodiacetic acid was prepared by heating 2–5 $\mu$ Ci of $Co^{57}Cl_2$ in the presence of 1 ml (20 mg/ml) of a solution of the compound (pH 4–5) for 1 hour at 100° C. The chelate was chromatographed and biodistribution studies carried out using the procedure of Example 8. At 30 minutes, 28% of the injected dose appears in the liver and 12% in the intestines.

EXAMPLE 12

The technetium-99m chelate of 10-carboxydecyliminodiacetic acid was prepared according to the stannous chloride reduction method of Examples 2, 3 and 8. The product was chromatographed in saline. >98% the material had an $R_f=1$. Biodistribution studies of the chelate according to Example 8 in ten 25 g mice showed rapid blood clearance with less than 6% of the injected dose remaining in the blood at 60 minutes. Radioactivity was eliminated through both kidneys and liver with persistent activity noted in the liver and lungs.

EXAMPLE 13

The technetium-99m chelate of N-(o-bromobenzyl) iminodiacetic acid was prepared by the stannous chloride reduction method described in Examples 2, 3 and 8. The product was paper chromatographed in saline (98% had an $R=1$.) Biodistribution studies carried out on twelve 25 g mice according to the procedure of Example 8 showed rapid blood clearance (less than 5% remainig at 60 minutes) with a high uptake in the liver (40%) and intestines (30%) at 30 minutes.

EXAMPLE 14

The procedure of Example 11 was followed to prepare the cobalt-57 chelate of methyliminodiacetic acid.

EXAMPLE 15

The procedure of Example 9 was followed to prepare the gallium-67 chelate of methyliminodiacetic acid. Biodistribution studies carried out according to the procedure of Example 8 showed rapid renal clearance.

EXAMPLE 16

The stannous chloride reduction procedure of Examples 2, 3 and 8 was employed to prepare the technetium-99m chelate of 5,7-diiodo-8-hydroxyquinoline.

EXAMPLE 17

The stannous chloride reduction method of Examples 2, 3 and 8 was used to prepare the technetium-99m chelate of 2,6-pyridinedicarboxylic acid.

We claim:
1. A chelate of technetium-99m, cobalt-57, gallium-67, gallium-68, indium-111 or indium-113m and a substituted iminodiacetic acid.
2. A chelate of technetium-99m cobalt-57, gallium-67, gallium-68, indium-111 or indium-113m and an 8-hyroxyquinoline.
3. A composition comprising a mixture of the technetium-99m chelate of claim 1 and the stannous chelate of said chelating agent.
4. A composition comprising a mixture of the technetium-99m chelate of claim 1, the stannous chelate of said chelating agent and said chelating agent.
5. The chelate of claim 1 wherein said iminodiacetic acid chelating agent is N-methyliminodiacetic acid, N-[N'-(2,6-dimethylphenyl) carbamoylmethyl] iminodiacetic acid, N-(10-carboxydecyl) iminodiacetic acid, N-(O-bromobenzyl) iminodiacetic acid, N-[3-(1-naphthyloxy)-2-hydroxypropyl] iminodiacetic acid, nitrilo-triacetic acid or 2,6-pyridinedicarboxylic acid.
6. N-[N'(2,6-dimethylphenyl) carbamoylmethyl] iminodiacetic acid.
7. A method of external imaging which includes the intravenous administration of a solution adapted for intravenous administration containing the chelate of claim 1.

8. A method of external imaging which includes the intravenous administration of a solution adapted for intravenous administration containing the chelate of claim 2.

9. A method of preparing the chelate of claim 1 comprising reacting said radio-isotope with said chelating agent.

10. The method of claim 9 wherein said radioisotope is technetium-99m.

11. The method of claim 10 wherein said chelate is prepared by reducing a pertechnetrate in the presence of said chelating agent.

12. The method of claim 11 wherein said reduction is effected utilizing stannous chloride as a reducing agent.

13. A method of preparing the chelate of claim 2 comprising reacting said radio-isotope with said chelating agent.

* * * * *